(12) United States Patent  
Greiner et al.

(10) Patent No.: US 10,271,729 B2  
(45) Date of Patent: Apr. 30, 2019

(54) MULTIPLE INDEPENDENT AUDIO SPHERES FOR PATIENT MONITOR

(71) Applicant: KONINKLIJKE PHILIPS N.V., Eindhoven (NL)

(72) Inventors: Harald Greiner, Nufringen (DE); Wilhelm Meier, Herrenberg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 15/553,610

(22) PCT Filed: Mar. 7, 2016

(86) PCT No.: PCT/IB2016/051263  
§ 371 (c)(1),  
(2) Date: Aug. 25, 2017

(87) PCT Pub. No.: WO2016/157007  
PCT Pub. Date: Oct. 6, 2016

(65) Prior Publication Data  
US 2018/0333050 A1 Nov. 22, 2018

Related U.S. Application Data

(60) Provisional application No. 62/139,160, filed on Mar. 27, 2015.

(51) Int. Cl.  
*A61B 5/00* (2006.01)  
*G16H 40/67* (2018.01)  
*G06F 19/00* (2018.01)

(52) U.S. Cl.  
CPC ............ *A61B 5/002* (2013.01); *A61B 5/7405* (2013.01); *A61B 5/746* (2013.01); *A61B 5/7445* (2013.01); *G16H 40/67* (2018.01); *G06F 19/3418* (2013.01)

(58) Field of Classification Search  
CPC ..... A61B 5/002; A61B 5/0022; A61B 5/1117; A61B 5/1128; G06F 19/00; G06F 19/30;  
(Continued)

(56) References Cited

U.S. PATENT DOCUMENTS 5,319,355 A 6/1994 Russek  
8,380,271 B2 2/2013 McCutcheon  
(Continued)

FOREIGN PATENT DOCUMENTS

EP 2289393 3/2011  
EP 2775463 9/2014  
WO 2014207597 12/2014

*Primary Examiner* — Van T Trieu

(57) ABSTRACT

A patient monitoring system includes a patient data acquisition system (12) to acquire patient data via patient physiological sensors (28). A first patient monitor display (16) and first audio system (18) is disposed inside a patient room. A second patient monitor display (20) and audio system (22) is disposed outside the patient room. A control system (14) outputs acquired patient data via at least one of the first patient monitor display and the second patient monitor display and outputs a patient audio monitor signal (60) generated based at least in part on acquired patient data using at least one of the first and second audio systems (18, 22). The control system (14) provides a first audio configuration (42) for operating the first audio system (18) and a second audio configuration (44) for operating the second audio system (22).

15 Claims, 4 Drawing Sheets

(58) Field of Classification Search
CPC .......... G06F 19/3074; G06F 19/30781; G06F 19/30846; G06F 19/32; G06F 19/324; G06F 19/3418; G16H 40/00; G16H 40/20; G16H 40/40; G16H 40/60; G16H 40/63; G16H 40/67
See application file for complete search history.

(56) References Cited

U.S. PATENT DOCUMENTS

| | | |
|---|---|---|
| 2007/0109115 A1 | 5/2007 | Kiani |
| 2009/0326340 A1 | 12/2009 | Wang |
| 2012/0126984 A1 | 5/2012 | Gilham |
| 2014/0142963 A1 | 5/2014 | Hill |
| 2014/0324451 A1* | 10/2014 | Pesot .................. A61B 5/0006 705/2 |
| 2015/0033295 A1* | 1/2015 | Huster ................... G06F 21/44 726/4 |
| 2015/0109442 A1* | 4/2015 | Derenne ................ G16H 80/00 348/143 |
| 2017/0249432 A1* | 8/2017 | Grantcharov ....... H04L 63/0272 |
| 2018/0122506 A1* | 5/2018 | Grantcharov ....... G06F 19/3481 |

* cited by examiner

MULTIPLE INDEPENDENT AUDIO SPHERES FOR PATIENT MONITOR

CROSS REFERENCE TO RELATED APPLICATIONS

This application is the U.S. National Phase application under 35 U.S.C. § 371 of International Application No. PCT/IB2016/051263, filed Mar. 7, 2016, published as WO 2016/157007 on Oct. 6, 2016, which claims the benefit of U.S. Provisional Patent Application No. 62/139,160 filed Mar. 27, 2015. These applications are hereby incorporated by reference herein.

FIELD

The following relates generally to medical monitoring devices, medical monitoring audio and visual systems, and related arts. However, it is to be understood that it also finds application in other usage scenarios and is not necessarily limited to the aforementioned application.

BACKGROUND

A patient monitor for use in a critical care unit typically includes inputs for various physiological (or vital sign) sensors, such as electrocardiograph (ECG) or other cardiac monitoring sensor(s), blood pressure sensor, peripheral capillary oxygen saturation ($SpO_2$) sensor, a respiration sensor, and so forth, as well as a display device for displaying vital sign readings in real time and/or trend lines plotting recent readings versus time, and an audio system for outputting alarms as well as other audio information such as simulated button clicks when users press displayed soft buttons. The patient monitor may also monitor important variables of therapeutic systems such as fluid infusion, air flow during mechanical respiration, or so forth. Conventionally, the patient monitor is a self-contained unit located in the patient room with vital sign sensors in wired connection with the patient monitor, although wireless connectivity is being increasingly leveraged to reduce the quantity of wiring around the patient.

A difficulty with this arrangement is that audio alarms output by the patient monitor may disturb or alarm the patient. Various measures may be taken to reduce patient noise disturbance, such as allowing audio alarms to be set to a low volume. However, functionality of the patient monitor audio system is of high importance to patient well-being, with some alarms being as life-critical in nature, and as such audio alarms of the patient monitor should not be allowed to be turned off or disabled to the point of compromising patient safety. Additionally, the audio system of the patient monitor may include some self-monitoring capability, e.g. of the volume level, or a speaker electric current sensor or so forth, in order to detect any audio system failure—an audio failure may be indicated by a flashing warning displayed on the monitor, or in extreme cases by having the monitor go blank.

Another difficulty with placement of the patient monitor in the patient room is that it is not readily observed by medical personnel, except during intermittent visits to the patient. Thus, a doctor or a nurse may not be able to hear/see an alarm if they are in another room away from the patient room. One way this is addressed is by employing large patient room windows, so that medical personnel in the aisle can view the patient and patient monitor from the aisle. This is an imperfect solution, since the patient monitor may be relatively far away and may be angled away from the window, or reflections at the window may obscure view of the patient monitor display. Such windowing also does not address perceptibility of audio alarms.

Another partial solution is to provide one or more secondary monitors, for example a monitor located in the aisle, and/or mirroring the patient monitor at the nurses' station, and/or providing an application program ("app") loaded onto a smartphone or other mobile device carried by the patient's nurse. Such secondary monitors are generally not required to meet the strict reliability requirements of a life-critical patient monitor. In such systems, medical personnel are sometimes able to turn off various alarms, or "mute" the device entirely (e.g. a cellphone set to "silent" mode), and wireless connectivity may be lost without notice.

Another difficulty is that there may be audio interference or overlap between the patient room monitor and the aisle monitor. This adds unnecessary noise and possible confusion to the critical care environment. An alternative is to not provide the aisle monitor with audio, but this reduces its effectiveness in alerting medical personnel.

The following provides new and improved methods and systems which overcome the above-referenced problems and others.

BRIEF SUMMARY

Conventional patient monitor displays are visible in the patient room, and is usually also visible from the aisle outside the patient room through the glass room window. Additionally or alternatively, a separate monitor display may be located in the aisle outside the patient room, which mirrors the display of the in-room monitor. This aisle monitor display may also include soft buttons or other user inputs again mirroring those of the in-room patient monitor.

As a further known extension, patient monitor alarms may be mirrored at the nurses' station, and/or via a pager carried by the nurse assigned to the patient. These, however, are considered "secondary" systems and are not required to meet the strict reliability requirements of the "primary" audio system of the in-room patient monitor. These secondary audio systems also usually provide less information, for example only sounding for life-critical ("red") alarms. A failure of a secondary audio system is not considered a safety-critical event.

Medical personnel may wish to have the primary audio sphere extend in a distributed fashion outside of the patient room. Most commonly, it may be desired to extend it into the aisle outside the patient room, where nurses are commonly present. As another example, in a quarantine the primary audio sphere might be extended to a non-sterile monitoring area. One way to extend the primary audio sphere is simply to increase the volume of the in-room monitor audio system so it can be heard in the aisle—but this creates a noisy critical care unit and is disturbing to the patient.

Various improvements are disclosed herein.

In some embodiments, independent primary audio systems (or spheres), e.g. the usual in-room audio system and a separate aisle audio system, are provided. This independent aisle audio system also serves as a primary audio system, and as such should meet the same safety constraints as the in-room patient monitor audio system. The in-room and aisle primary audio systems, while independent, are linked to ensure that at least one primary audio system is operative at all times. If for example, the nurse turns off the in-room audio system (or portions of this system, e.g. the yellow alarms while leaving the red alarms active in-room)

to provide a quiet environment for the patient, then these disabled in-room alarms should be automatically enabled on the aisle primary audio system.

In other illustrative embodiments, each primary audio system should be individually configurable. For example, the aisle system may have higher volume settings so as to be heard in the usually noisier aisle environment. Similarly, different audio sounds may be used for a given alarm in the different primary audio spheres. In one approach, each primary audio sphere has its own default audio configuration, and the nurse can then easily switch between the two audio spheres, or active both simultaneously. The nurse preferably can also adjust at least some of the default audio values to accommodate specific situations.

In accordance with one aspect, a patient monitoring system for monitoring a patient is provided. The patient monitoring system includes a patient data acquisition system configured to acquire patient data via a plurality of patient physiological sensors. A first patient monitor display is disposed inside a patient room. A second patient monitor display is disposed outside the patient room. A first audio system is disposed with the first patient monitor display inside the patient room. A second audio system is disposed with the second patient monitor outside the patient room. A control system is configured to output patient data acquired by the patient data acquisition system via at least one of the first patient monitor display and the second patient monitor display and further configured to output a patient audio monitor signal generated based at least in part on patient data acquired by the patient data acquisition system using at least one of the first and second audio systems. The control system includes one or more processors programmed with a first audio configuration for operating the first audio system and a second audio configuration for operating the second audio system.

In accordance with another aspect, a patient monitoring system for monitoring a patient is provided. The patient monitoring system includes a patient data acquisition system configured to acquire patient data via a plurality of patient physiological sensors. The patient monitoring system also includes a first patient monitor display and a second patient monitor display. A first audio system is built into or operatively connected with the first patient monitor display. A second audio system is built into or operatively connected with the second patient monitor. A control system programmed to output patient data acquired by the patient data acquisition system via at least one of the first patient monitor display and the second patient monitor display, and output a patient audio monitor signal generated based at least in part on patient data acquired by the patient data acquisition system using at least one of the first and second audio systems. The primary audio control system includes one or more processors programmed to control a first audio configuration and a separate second audio configuration associated with a corresponding one of the first and second audio systems.

In accordance with another aspect, a method for monitoring a patient in a patient room is provided. A patient monitor signal is outputted using at least one of: (1) an audio system disposed inside of a patient room and a patient monitor display disposed inside of the patient room, and (2) an audio system disposed outside of the patient room and a patient monitor display disposed outside of the patient room. The generating uses a first audio configuration when outputting the patient monitor signal using the audio system disposed inside the patient room and a second audio configuration when outputting the patient monitor signal using the audio system disposed outside the patient room. The audio system disposed inside the patient room is electronically linked and the audio system disposed outside the patient room to ensure that the patient monitor signal is output using at least one of the audio system disposed inside the patient room and the audio system disposed outside the patient room.

One advantage resides in a medical monitoring system with independent audio/visual spheres disposed in separate rooms.

Another advantage resides in a medical monitoring system that can transfer operation from one audio/visual sphere to another audio/visual sphere.

Another advantage resides in a medical monitoring system with independent audio/visual systems that are individually configurable.

Still further advantages of the present disclosure will be appreciated to those of ordinary skill in the art upon reading and understanding the following detailed description.

BRIEF DESCRIPTION OF THE DRAWINGS

The present disclosure may take form in various components and arrangements of components, and in various steps and arrangements of steps. The drawings are only for purposes of illustrating the preferred embodiments and are not to be construed as limiting the present disclosure.

DETAILED DESCRIPTION

Figure 1:
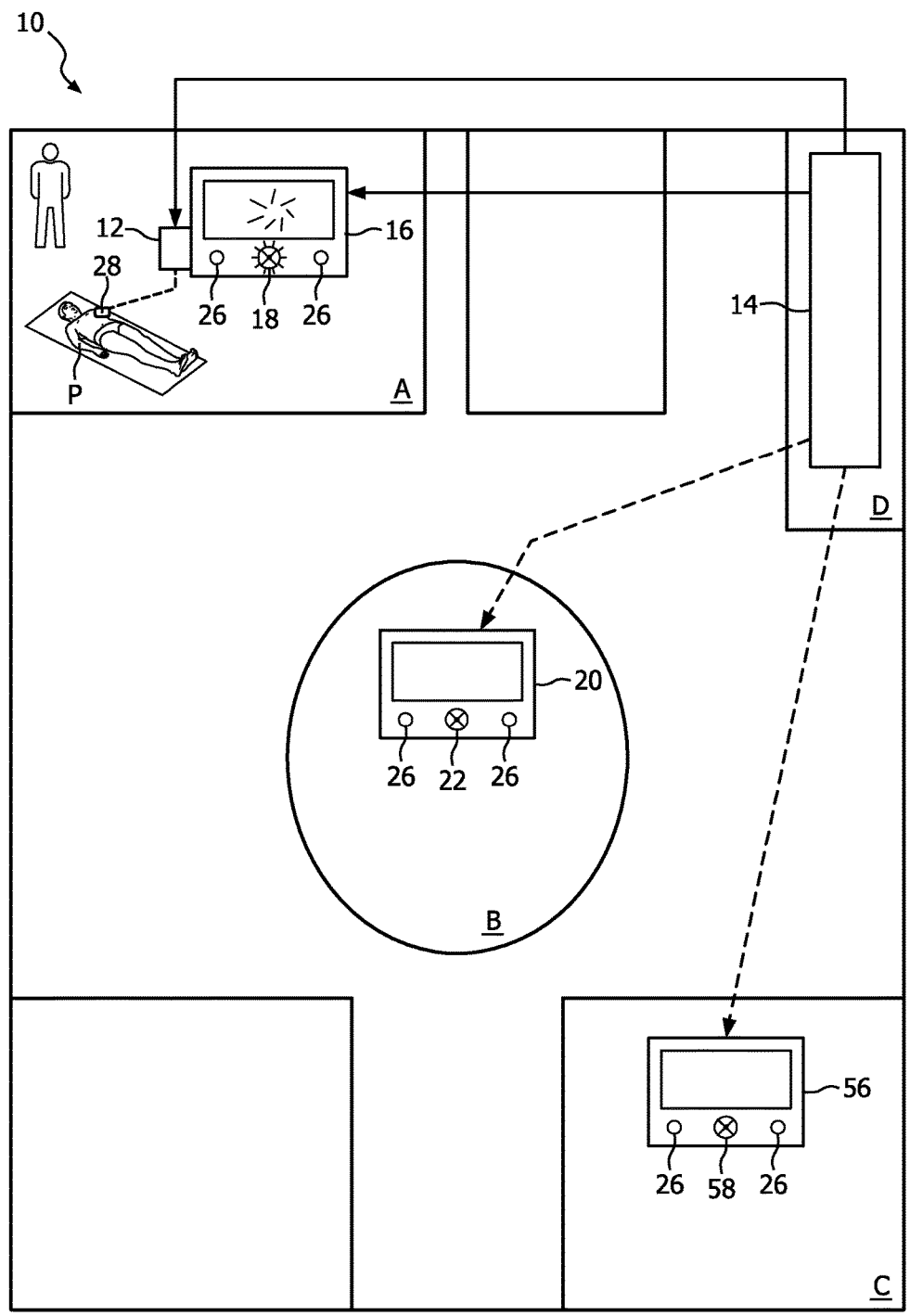
FIG. 1 diagrammatically shows a plan view of a patient monitoring system in one embodiment of the present disclosure.

With reference to FIG. 1, a patient monitoring system for monitoring a patient P located in a patient room A is shown. The patient monitoring system includes a patient data acquisition system 12 located with the patient P in the patient room A to acquire patient data (e.g. vital signs such as ECG, blood pressure, respiration, and so forth). A control system 14 controls distributed human-perceptible visual/audio output of patient data acquired by the acquisition system 12 at various locations, such as via a patient monitor display 16 and associated audio system 18 located in the patient room A, or at similar output video/audio devices located elsewhere, such as in a hallway or aisle B outside the patient room A, and/or at a break room C, or so forth. Commonly, the audio system 18 is built into the patient monitor display 16 as a built-in speaker or built-in speaker system; however, it is alternatively contemplated for an audio system to be operatively connected with, but physically separate from, a patient monitor display. For example, in the hallway B it may be appropriate for the audio system to comprise a public address (PA) speaker that outputs audio generated in association with the hallway patient monitor display. Advantageously, the control system 14 is configured to regulate operation of selected audio and video components of the patient monitoring system, as described in more detail below.

Figure 2:
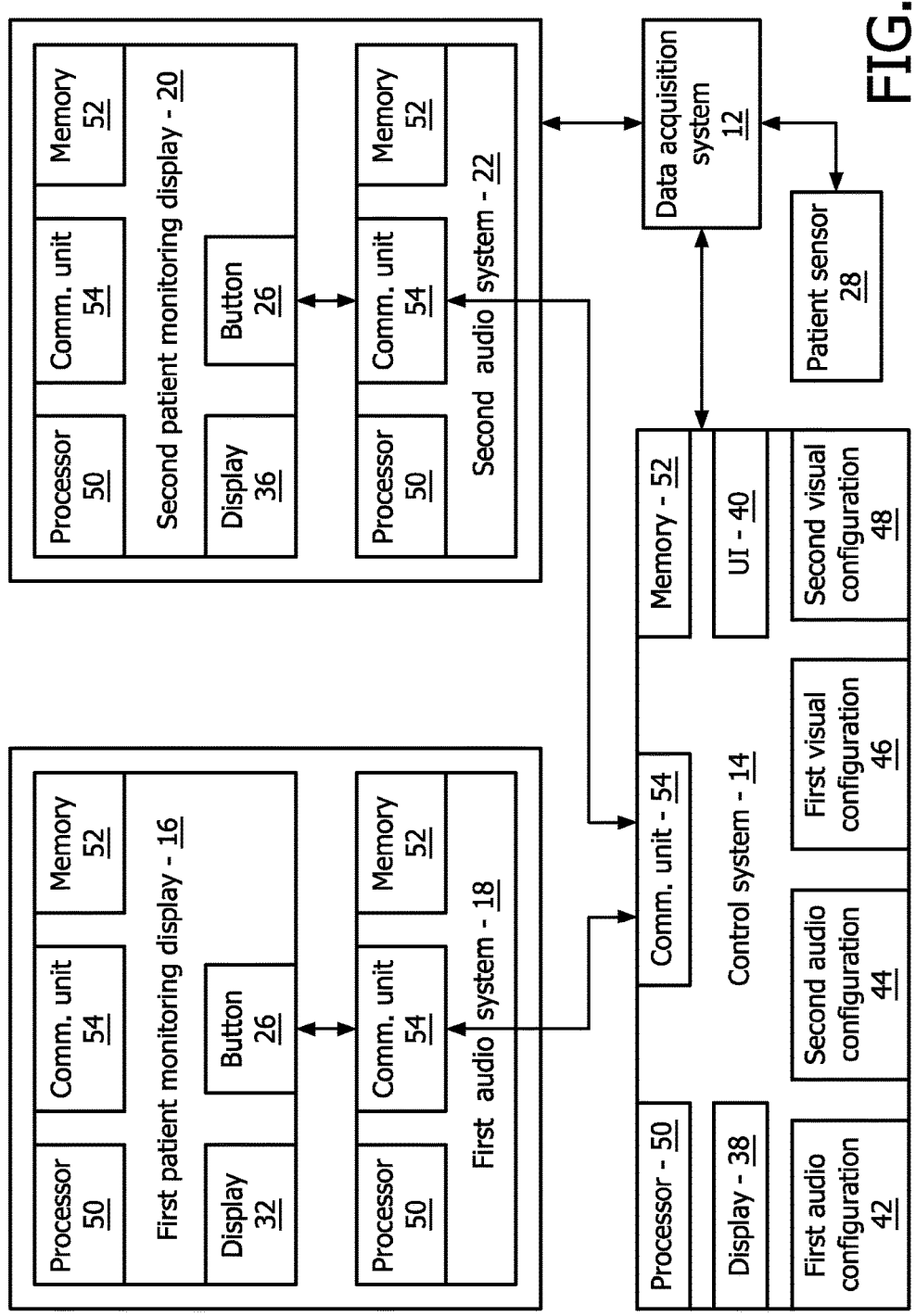
FIG. 2 a schematic view of the patient monitoring system of FIG. 1.

With continuing reference to FIG. 1 and with further reference to FIG. 2, a first patient monitor display 16 has a built-in or operatively connected first audio system 18. Similarly, a second patient monitor display 20 has a built-in or operatively connected second audio system 22. Patient data are acquired by the patient data acquisition system 12 via various patient sensors (ECG, blood pressure sensors, respiration sensors, $SpO_2$ sensors, or so forth, generally represented as block 28) are formatted by the acquisition system 12 as a real-time numeric value, trend line (e.g. ECG lead trace(s), or $SpO_2$ trace as a function of time), or so forth. The acquisition system 12 may also trigger an alarm if a vital sign goes outside of a permissible range, usually indicating a possible deterioration of patient condition. Thus, for example, the acquisition system 12 may output an alarm signal if the heart rate exceed 150 beats per minute (or some other upper threshold), or falls below 50 beats per minute (or some other lower threshold). Optionally, the patient data may include patient data other than vital signs, such as an infusion rate of fluid delivered to the patient by an intravenous infusion pump.

The illustrative first patient monitor display 14 may optionally include a user interface 26 such as at least one illustrated button or switch 26, or some other physical user interfacing device (e.g. a keyboard, trackball) and/or one or more soft keys (displayed on the display area of the monitor display 14 which comprises a touch-sensitive display in order to detect a finger press on the soft key).

The second patient monitor display 20 located in the hallway or aisle B can be similarly configured as the first patient monitor display 14. For example, the second patient monitor display 20 includes at least one button or switch or other user interfacing device(s) 26.

The first and second audio systems 18 and 22 are associated with the first and second patient monitor displays 18, 20 and may, for example, each be a built-in speaker, an external speaker (e.g. aisle PA speaker), or any other suitable device for outputting a sound, tone, beep, or buzz. The first audio system 18 is located in the patient room A and the second audio system 22 is located outside of the patient room A such as in the aisle B.

The patient monitoring system of FIGS. 1 and 2 provides a distributed output in that visual/audio patient data may be output via the first patient monitor display 16 and built-in or operatively connected first audio system 18; and alternatively or additionally visual/audio patient data may be output via the second patient monitor display 20 and built-in or operatively connected first audio system 22. This distributed output is enabled by way of the centralized control system 14 stores configurations associated with the respective first output system 16, 18 and second output system 20, 22. These typically include one or more suggested or entered patient monitoring options/orders as a function of the patient data (i.e. from the patient sensor 28) and the activation/deactivation of the components of the patient data acquisition system 12. The control system 14 includes a user interface with a display 38 (such as a CRT display, a liquid crystal display, a light emitting diode display, and the like) to display the configurations and a user input device 40 such as a keyboard and a mouse, for the nurse or other user to input and/or modify and/or select an output choice and configuration for each output. The control system 14 regulates operation of the patient monitoring system. For example, the control system 14 can transfer operation of one of the first and second patient monitor displays 16 and 20 and/or one of the first and second audio systems 18 and 22 to the other of the first and second patient monitor displays 16 and 20 and/or the first and second audio systems 18 and 22. To do so, the control system 14 advantageously stores in a non-transitory memory (e.g. a solid state memory, magnetic hard drive, or so forth) a first audio configuration 42 associated with the first audio system 16, a second audio configuration 44 associated with the second audio system 24, a first visual configuration 46 associated with the first patient monitor display 14, and a second visual configuration 48 associated with the second patient monitor display 20, as described in more detail below.

The control system 14 include one or more electronic processors 50 executing computer executable instructions embodying the foregoing functionality, where the computer executable instructions are stored on one or more non-transitory memories 52 associated with the processors 50. Further, the components of the control system 14 include one or more communication units 54 providing the one or more processors 50 with an interface via which to communicate with the various patient data output devices 16, 18, 20, 22.

The control system 14 is illustrated as a component separate from the acquisition system 12 and from the output systems 16, 18 and 20, 22. However, it will be appreciated that these systems may be variously integrated.

For example, in one contemplated embodiment, the patient monitor located inside the patient room A comprises a computer or other electronic data processing device with sensor input circuitry (e.g. sensor input couplings, analog-to-digital converters for connecting analog sensors, and so forth) that implements the patient data acquisition system 12, and additionally includes an integral or connected display device located in the patient room A which implements the first patient monitor display 16 and further implements the first audio system 18 via a built-in speaker. In this embodiment, the electronic processor (e.g. microprocessor or multi-core processor) of the computer or other electronic data processing device located in the patient room A is further programmed to implement the control system 14, so that the user input device(s) 26 and display 32 implement the display 38 and user interface 26 of the first patient monitor display 16 are the display 38 and user interface 40, respectively, of the control system 14. In this embodiment, the main unit of the patient monitor is located in the patient room A, and includes the acquisition system 12, the first patient monitor display 16 and audio system 18, and the control system 14, the latter of which enables additional remote display/audio components such as the illustrative second patient monitor display 20 and audio system 22 to be connected.

Referring to FIG. 1, the control system 14 is configured to output at least a patient audio monitor signal using at least one of the first and second audio systems 18 and 22. To do so, the first and second audio configurations 42 and 44 each have predefined parameters. The predefined parameters of the first audio configuration 42 are different from the predefined parameters of the second audio configuration 44. In one example, the predefined parameters of each of the first and second audio configurations 42 and 44 can include alarm sound type and alarm sound volume. Each of the predefined parameters is individually configurable. Stated another way, the alarm sound type of the first audio configuration 42 can be a first type of sound (e.g., a high-pitched "ping" sound) while the alarm sound type of the second audio configuration 44 can be a second type of sound (e.g., a low-pitched "boom" sound) that is different from the first type of sound.

In other embodiments, the control system 14 is configured to output at least a patient visual monitor signal using at least one of the first and second patient monitor displays 16 and 20. To do so, the first and second visual configurations 46 and 48 each have predefined parameters. The predefined parameters of the first visual configuration processor 46 are different from the predefined parameters of the second visual configuration processor 48. In one example, the predefined parameters of each of the first and second visual configuration processors 46 and 48 can include color and intensity. Each of the predefined parameters is individually configurable. Stated another way, the color of the first visual configuration processor 46 can be a first type of color (e.g., yellow) while the color of the second visual configuration processor 48 can be a second type of color (e.g., red) that is different from the first type of color.

Figure 3:
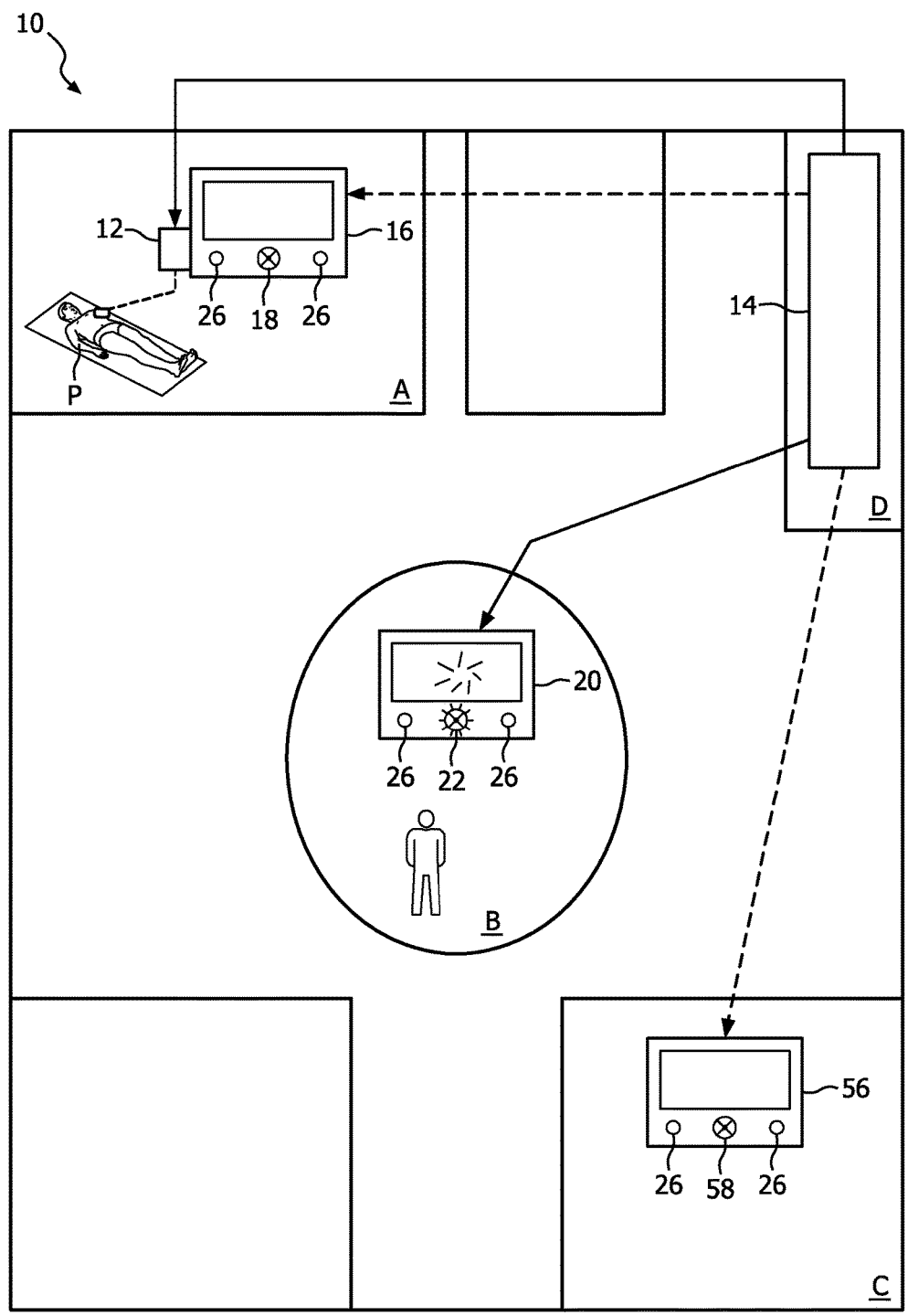
FIG. 3 shows the patient monitoring system of FIG. 1 in a alternate configuration.

As shown in FIGS. 1 and 3, the first patient monitor display 16 and the first audio system 18 are disposed in a first area (i.e., a patient's room A), while the second patient monitor display 20 and the second audio system 22 are disposed in a second area outside of the first area (i.e., an area outside the patient room, such as a nurses' station B). In some embodiments, a third patient monitor display 56 and a third audio system 58 can be disposed in a third area (i.e., a break room C). The third patient monitor display 56 and the third audio system 58 can be similarly configured as the first/second patient monitor displays 16/20 and the first/second audio systems 18/22, respectively. The third patient monitor display 56 and the third audio system 58 are operatively connected to the control system 14 (i.e., via corresponding configuration processors (not shown)). The control system 14 can be located in any suitable area (e.g., a doctor's office, a server room D, the nurses' station B, the break room C, and the like), as long as the control system 14 is in communication with each of the patient monitor displays 16, 20, and 56 and each of the audio systems 18, 22, and 58.

In one example embodiment, the control system 14 is configured to transfer operation of one of the first and second audio systems 18 and 22 (or the third audio system 58, when present) from the other of the first and second audio systems 18 and 22 such that at least one of the first and second audio systems 18 and 22 is continuously activated. This is shown schematically in FIG. 1 with a solid line extending from the control system 14 to the first patient monitor display/first audio system 16/18 and dashed lines extending from the control system 14 to each of to the second patient monitor display/second audio system 20/22 and the third patient monitor display/third audio system 56/58. For example, the first audio system 18 can be turned on by a user (i.e., a nurse) when the nurse enters the patient room A by pressing one of the buttons 26 on the first patient monitor display 16. This is shown schematically in FIG. 1 with dashed lines extending from the first audio system 18. Consequently, the nurse can hear a patient monitor audio signal (e.g. an audio alarm) 60 from the first audio system 18 while the nurse is in the patient room A (i.e., during cleaning of the room or tending to the patient).

Figure 4:
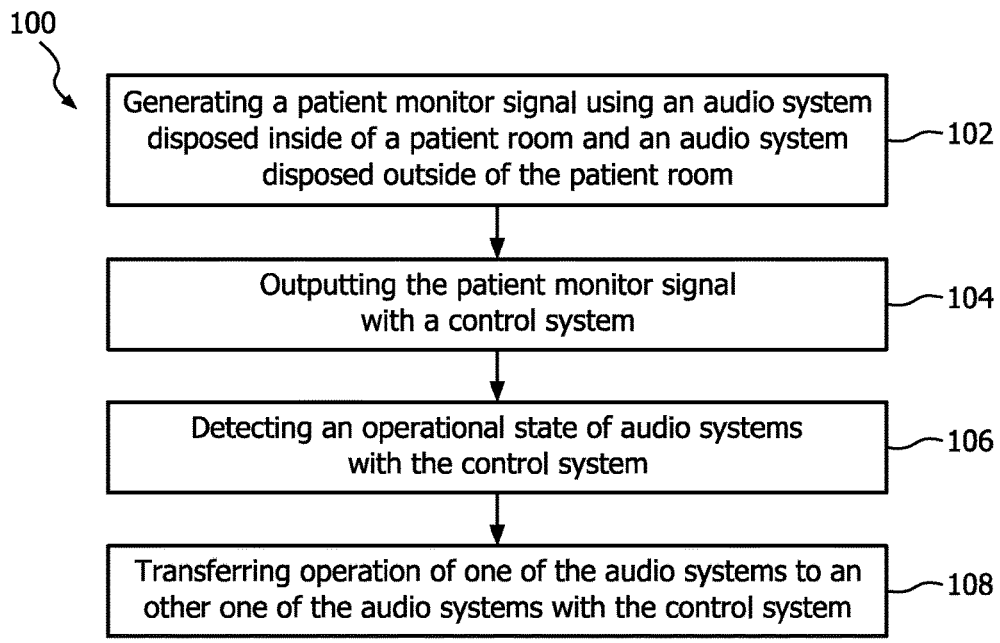
FIG. 4 shows a first exemplary flow chart of the patient care monitor of FIG. 1.

When the nurse leaves the patient room A, in one example, the nurse can leave the first audio system 18 in its current state (i.e., so that the alarm 60 is still emitted in the patient room A) so that the nurse can still hear the alarm 60 if he or she remains close to the patient room A (i.e., in the hallway or another adjacent patient room). In another example, as shown in FIG. 4, the nurse can press or activate one of the buttons 26 so that audio output of the patient data acquisition system 12 (and any other audio output by the patient monitor, such as soft key "clicks") is transferred from the first audio system 18 to the second audio system 22 (or the third audio system 58) so that the alarm 60 is emitted via the second or third audio system 22 or 58 at either the nurses' station B or the break room C. This is shown schematically in FIG. 3 with a solid line extending from the control system 14 to the second patient monitor display/second audio system 20/22 and dashed lines extending from the control system 14 to each of to the first patient monitor display/first audio system 16/18 and the third patient monitor display/third audio system 56/58. Advantageously, the transfer of the alarm 60 from the first audio system 18 to a different audio system 22 or 58 reduces the noise on the patient floor, thereby increasing the comfort of the user while allowing the medical staff to monitor patients when they are not in a specific patient's room.

In another example embodiment, the control system 14 is configured to detect a failure of at least one of the first and second audio systems 18 and 22 (or the third audio system 58, when present). For example, the first, second, or third audio systems 18, 22, or 58 can become damaged (i.e., by wear and tear, being dropped or bumped, having liquid spilled on it, and the like) or can malfunction (i.e., by interference, a bad connection with the control system 14, and the like). The control system 14 continuously detects an operational state of the first, second, and third audio systems 18, 22, and 58. In one example, one of these operational states can be a "failure" operational state when any of the above-listed conditions occur. If one of the first, second, or third audio systems 18, 22, or 58, the control system 14 automatically transfers operation of the audio output of the patient data acquisition system 12 (and any other audio output by the patient monitor, such as simulated soft key "clicks") from the failed audio system (i.e., the first audio system 18, as shown in FIG. 1) to another audio system (i.e., the second audio system 22, as shown in FIG. 3) so that the alarm 60 is generated and outputted with the "active" audio system. Advantageously, the control system 14 ensures that at least one of the audio systems 18, 22, and 58 is continuously active (i.e., outputting the alarm 60) even when at least one of the other audio systems has failed.

Similarly, in a further example embodiment, the control system 14 is configured to transfer operation of one of the first and second patient monitor displays 16 and 20 (or the third audio system 58, when present) from the other of the first and second patient monitor displays 16 and 20 such that at least one of the first and second patient monitor displays 16 and 20 is continuously activated. This is shown schematically in FIG. 1 with a solid line extending from the control system 14 to the first patient monitor display/first audio system 16/18 and dashed lines extending from the control system 14 to each of to the second patient monitor display/second audio system 20/22 and the third patient monitor display/third audio system 56/58. For example, the first patient monitor display 16 can be turned on by a user (i.e., a nurse) when the nurse enters the patient room A by pressing one of the buttons 26 on the first patient monitor display 16. This is shown schematically in FIG. 1 with dashed lines extending from the first patient monitor display 16. Consequently, the nurse can hear a patient monitor visual signal (e.g. a red screen visual alarm) 62 from the first patient monitor display 16 while the nurse is in the patient room A (i.e., during cleaning of the room or tending to the patient).

When the nurse leaves the patient room A, in one example, the nurse can leave the first patient monitor display 16 in its current state (i.e., so that the alarm 62 is still emitted in the patient room A) so that the nurse can still hear the alarm 62 if he or she remains close to the patient room A (i.e., in the hallway or another adjacent patient room). In another example, the nurse can press or activate one of the buttons 26 so that display of patient data acquired by the patient data acquisition system 12 is transferred from the first patient monitor display 16 to the second patient monitor display 20 (or the third patient monitor display 56) so that the alarm 62 is emitted via the second or third audio system 20 or 56 at either the nurses' station B or the break room C. This is shown schematically in FIG. 3 with a solid line extending from the control system 14 to the second patient monitor display/second audio system 20/22 and dashed lines extending from the control system 14 to each of to the first patient monitor display/first audio system 16/18 and the third patient monitor display/third audio system 56/58. Advantageously, the transfer of the alarm 62 from the first patient monitor display 16 to a different patient monitor display 20 or 56 reduces the light on the patient floor, thereby increasing the comfort of the user while allowing the medical staff to monitor patients when they are not in a specific patient's room.

In another example embodiment, the control system 14 is configured to detect a failure of at least one of the first and second patient monitor displays 16 and 20 (or the third patient monitor display 56). For example, the first, second, or third patient monitor displays 16, 20, or 56 can become damaged (i.e., by wear and tear, being dropped or bumped, having liquid spilled on it, and the like) or can malfunction (i.e., by interference, a bad connection with the control system 14, and the like). When any of these conditions occur, the control system 14 detects an operational state of the first and second patient monitor displays 16 and 20. In one example, one of these operational states can be a "failure" operational state. If one of the first and second patient monitor displays 16 and 20 fails, the control system 14 automatically transfers display of patient data acquired by the patient data acquisition system 12 from the failed patient monitor display (i.e., the first patient monitor display 16, as shown in FIG. 1) to another patient monitor display (i.e., the second patient monitor display 20, as shown in FIG. 3) so that the alarm 62 is generated and outputted with the "active" patient monitor display. Advantageously, the control system 14 ensures that at least one of the patient monitor displays 16, 20, and 56 is continuously active (i.e., outputting the alarm 62) even when at least one of the other patient monitor displays has failed.

With reference to FIG. 4, an example method 100 of monitoring a patient is diagrammatically shown. The method 100 includes the steps of: generating at least one patient monitor signal 60 using at least one of at least one audio system 18 disposed inside of a patient room and at least one audio system 22 disposed outside of the patient room in which the at least one patient monitor signal 60 including at least one predefined parameter (Step 102); outputting the patient monitor signal 60 based on the predefined parameters using at least one of the first and second audio systems 18, 22 with a control system 14 (Step 104); detecting an operational state of the at least one audio system 18, 22 with the control system 14 (Step 106); and transferring operation of one of the audio systems 18, 22 to another one of the audio systems 18, 22 with the control system 14 (Step 108).

Figure 5:
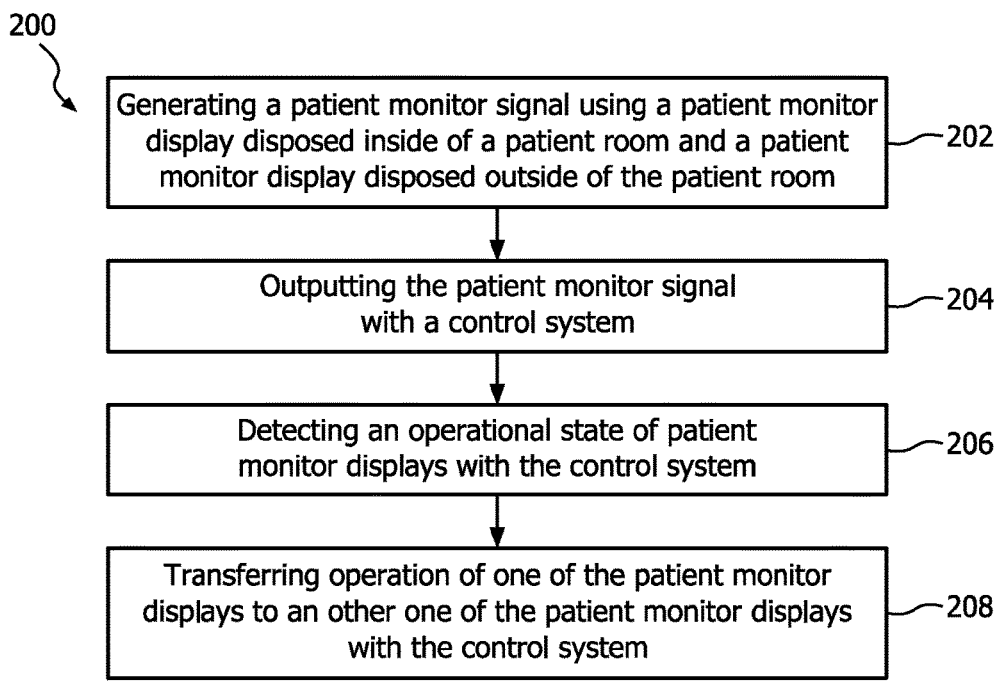
FIG. 5 shows a second exemplary flow chart of the patient care monitor of FIG. 1.

With reference to FIG. 5, an example method 200 of monitoring a patient is diagrammatically shown. The method 200 includes the steps of: generating at least one patient monitor signal 62 using at least one of at least one patient monitor display 16 disposed inside of a patient room and at least one patient monitor display 20 disposed outside of the patient room in which the at least one patient monitor signal 62 including at least one predefined parameter (Step 202); outputting the patient monitor signal 62 based on the predefined parameters using at least one of the patient monitor displays 16, 20 with a control system 14 (Step 204); detecting an operational state of the at least one patient monitor display 16, 20 with the control system 14 (Step 206); and transferring operation of one of the patient monitor displays 16, 20 to an other one of the patient monitor displays 16, 20 with the control system 14 (Step 208).

As used herein, a memory includes one or more of a non-transient computer readable medium; a magnetic disk or other magnetic storage medium; an optical disk or other optical storage medium; a random access memory (RAM), read-only memory (ROM), or other electronic memory device or chip or set of operatively interconnected chips; an Internet/Intranet server from which the stored instructions may be retrieved via the Internet/Intranet or a local area network; or so forth. Further, as used herein, a processor includes one or more of a microprocessor, a microcontroller, a graphic processing unit (GPU), an application-specific integrated circuit (ASIC), a field-programmable gate array (FPGA), personal data assistant (PDA), cellular smartphones, mobile watches, computing glass, and similar body worn, implanted or carried mobile gear; a user input device includes one or more of a mouse, a keyboard, a touch screen display, one or more buttons, one or more switches, one or more toggles, and the like; and a display device includes one or more of a LCD display, an LED display, a plasma display, a projection display, a touch screen display, and the like. Stated another way, the patient monitoring system 10 can be a non-transitory computer readable, storable medium carrying software to control a processor.

The invention has been described with reference to the preferred embodiments. Modifications and alterations may occur to others upon reading and understanding the preceding detailed description. It is intended that the invention be constructed as including all such modifications and alterations as they come within the scope of the appended claims or the equivalents thereof.

The invention claimed is:

1. A patient monitoring system for monitoring a patient, the patient monitoring system comprising:
   a patient data acquisition system configured to acquire patient data via a plurality of patient physiological sensors;
   a first patient monitor display;
   a second patient monitor display;
   a first audio system built into or operatively connected with the first patient monitor display;
   a second audio system built into or operatively connected with the second patient monitor display; and
   a control system programmed to:
      output patient data acquired by the patient data acquisition system via at least one of the first patient monitor display and the second patient monitor display;
      output a patient audio monitor signal generated based at least in part on patient data acquired by the patient data acquisition system using at least one of the first and second audio systems;
   wherein the control system includes one or more processors programmed to:

control a first audio configuration and a separate second audio configuration associated with a corresponding one of the first and second audio systems;

control a first visual configuration and a second visual configuration of the corresponding one of the first and second patient monitor displays; and transfer operation of one of the first and second patient monitor displays to the other of the first and second patient monitor displays such that at least one of the first and second patient monitor displays is continuously activated.

2. The patient monitoring system according to claim 1, wherein the control system is configured to:
detect an operational state of the outputting of the patient audio monitor signal; and
transfer the patient audio monitor signal from one of the first and second audio systems to the other of the first and second audio systems in response to detecting loss of an operational state of the outputting of the patient audio monitor signal.

3. The patient monitoring system according to claim 1, wherein:
the first audio system is built into the first patient monitor display; and
the second audio system is built into the second patient monitor display.

4. The patient monitoring system according to claim 1, wherein:
the first patient monitor display and the first audio system are disposed inside a patient room; and
the second patient monitor display and the second audio system are disposed outside the patient room.

5. The patient monitoring system according to claim 1, wherein the first and second audio configurations each have predefined parameters, the predefined parameters of the first audio configuration being different from the predefined parameters of the second audio configuration.

6. The patient monitoring system according to claim 5, wherein the predefined parameters of the first and second audio configurations includes alarm sound type and alarm sound volume, each of the predefined parameters being individually configurable.

7. The patient monitoring system according to claim 5, wherein the control system is configured to transfer the patient audio monitor signal from one of the first and second audio systems to the other of the first and second audio systems to ensure that the patient audio monitor signal is output by at least one of the first and second audio systems.

8. The patient monitoring system according to claim 1, wherein the primary audio control system is configured to detect a failure of at least one of the first and second audio systems.

9. The patient monitoring system according to claim 8, wherein the control system is configured to transfer operation of one of the first and second audio systems to the other of the first and second audio systems upon detection of the failure.

10. The patient monitoring system according to claim 1, further including a third audio system disposed outside of the patient room and spaced from the second audio system, the third audio system including a third patient monitor display controlled by the control system.

11. The patient monitoring system according to claim 1, wherein the control system further includes one or more processors programmed to control the first visual configuration and the second visual configuration of the corresponding one of the first and second patient monitor displays, the first and second visual configurations include at least one visual alarm with parameters including color and intensity.

12. The patient monitoring system according to claim 1, further comprising:
a patient data acquisition system configured to acquire patient data via a plurality of patient physiological sensors;
a first patient monitor display disposed inside a patient room;
a second patient monitor display disposed outside the patient room;
a first audio system disposed with the first patient monitor display inside the patient room;
a second audio system disposed with the second patient monitor outside the patient room;
a control system configured to output patient data acquired by the patient data acquisition system via at least one of the first patient monitor display and the second patient monitor display and further configured to output a patient audio monitor signal generated based at least in part on patient data acquired by the patient data acquisition system using at least one of the first and second audio systems;
wherein the control system includes one or more processors programmed with a first audio configuration for operating the first audio system and a second audio configuration for operating the second audio system.

13. The patient monitoring system according to claim 12, wherein the first and second audio configurations each have predefined parameters, the predefined parameters of the first audio configuration being independent from the predefined parameters of the second audio configuration.

14. A method for monitoring a patient in a patient room, the method comprising:
outputting a patient monitor signal generated using at least one of: an audio system disposed inside of a patient room and a patient monitor display disposed inside of the patient room, and an audio system disposed outside of the patient room and a patient monitor display disposed outside of the patient room;
wherein the generating uses a first audio configuration when outputting the patient monitor signal using the audio system disposed inside the patient room and a second audio configuration when outputting the patient monitor signal using the audio system disposed outside the patient room;
electronically linking the audio system disposed inside the patient room and the audio system disposed outside the patient room to ensure that the patient monitor signal is output using at least one of the audio system disposed inside the patient room and the audio system disposed outside the patient room;
wherein the generating uses a first visual configuration when outputting the patient monitor signal using the patient monitor display disposed inside the patient room and a second video configuration when outputting the patient monitor signal using the video system disposed outside the patient room;
electronically linking the video system disposed inside the patient room and the video system disposed outside the patient room to ensure that the patient monitor signal is output using at least one of the video system disposed inside the patient room and the video system disposed outside the patient room; and
transferring the patient audio monitor signal from one of the first and second audio systems to the other of the first and second audio systems to ensure that the patient audio monitor signal is output by at least one of the first and second audio systems such that at least one of the first and second audio systems is continuously activated.

15. The method of claim 14, further comprising:
providing a user interface via which a user can independently configure the first audio configuration used with the audio system disposed inside the patient room and the second audio configuration used with the audio system disposed outside the patient room.

* * * * *